United States Patent
Bock et al.

(10) Patent No.: US 6,437,123 B1
(45) Date of Patent: *Aug. 20, 2002

(54) TRIAZINE COMPOUNDS AND THEIR USE

(75) Inventors: Harald Reinhart Bock, Bordeaux (FR); Sally Anderson, Oxford (GB); Yoshimasa Fujita, Kashihara (JP); Andrew James Hudson, Abingdon (GB); Judy Megan Rorison, Cheltenham (GB); Michael Stuart Weaver, Cowley (GB)

(73) Assignee: Sharp Kabushiki Kaisha, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/299,995

(22) Filed: Apr. 27, 1999

(30) Foreign Application Priority Data

Apr. 30, 1998 (GB) ................................................ 9809143

(51) Int. Cl.$^7$ .................... C07D 251/24; C09K 19/52
(52) U.S. Cl. .................... 544/216; 136/252; 430/78; 252/299
(58) Field of Search ........................................ 544/216

(56) References Cited

U.S. PATENT DOCUMENTS 3,113,941 A * 12/1963 Johns et al. ............... 544/216

FOREIGN PATENT DOCUMENTS

WO 9310116 5/1993

OTHER PUBLICATIONS

A. P. Rudenko, et al., Oxidation of Aromatic Compounds. V. Oxidation of Substituted Benzonitriles and 2,4, 6–Triaryl–1, 3, 5–Triazines in the HSO$_3$F–PbO$_2$. Russian Journal or Organic Chemistry, vol. 32, No. 10, pp. 1447–1470, 1996.

Synthesis of S–Triazines. Synthesis: International Journal of Methods in Synthetic Organic Chemistry, No. 1, Jan. pp. 95–98, 1985.

A.P. Rudenko et al., Oxidation of Aromatic Compounds. V. Oxidation of Substituted Benzonitriles and 2,4, 6–Triaryl–1, 3, 5–Triazines in the HSO3f–Pb02, (Abstract).

A. Llobera et al., Synthesis of S–Triazines from Aromatic Aldehydes, (Abstract).

Abstract for 103156–86–1.

* cited by examiner

Primary Examiner—Mukund J. Shah
Assistant Examiner—Venkataraman Balasubramanian
(74) Attorney, Agent, or Firm—Renner, Otto, Boisselle & Sklar, LLP

(57) ABSTRACT

A compound of the present invention is a triazine compound of the general formula:

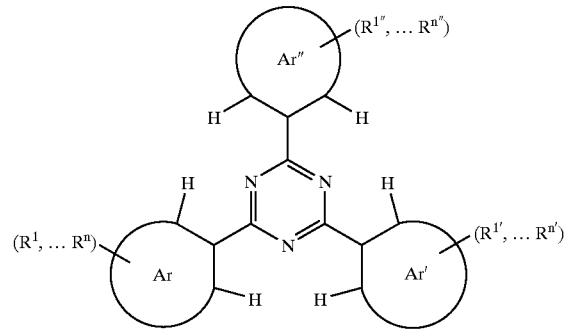

Figure 1:
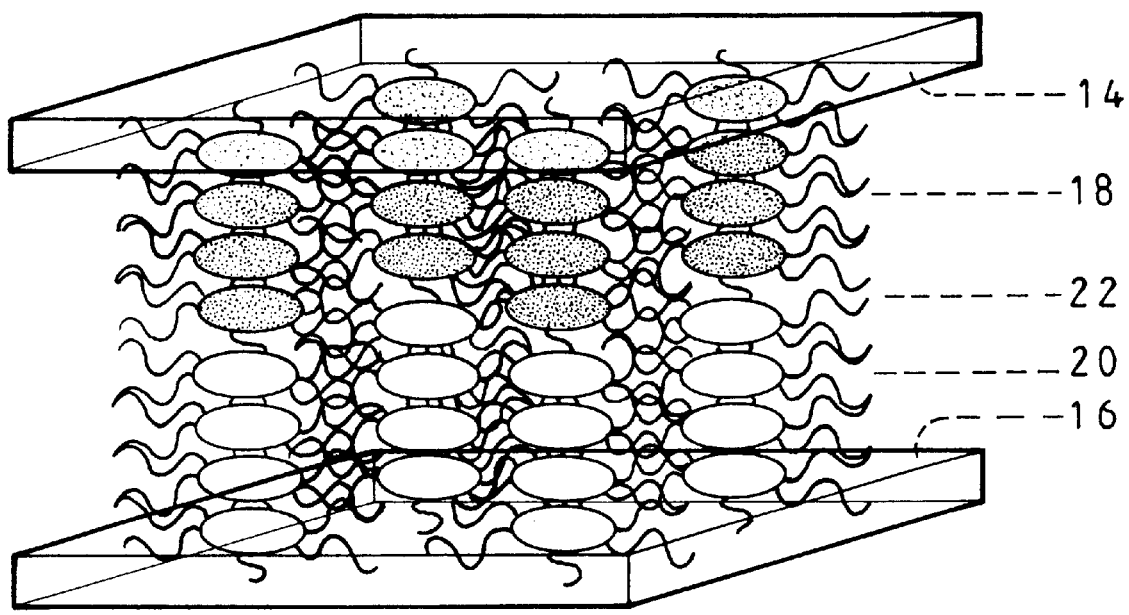

Ar, Ar' and Ar" are aromatic moieties which are conjugated to the triazine core and are the same or different. Each of $R^1$, $R^{1'}$, $R^{1''}$ to $R^n$, $R^{n'}$, $R^{n''}$, which may be the same or different, is an elongated flexible, at least partly aliphatic chain such as to impart liquid-crystalline or columnar crystalline properties to the compound or its mixtures. —($R^1$, ..., $R^n$), —($R^{1'}$, ..., $R^{n'}$) and —($R^{1''}$, ..., $R^{n''}$) indicate that there are up to n, n' and n" substituent groups R on respective Ar, Ar', Ar" moieties, where n, n' and n" are integers which do not exceed a number of available substituent positions on the respective Ar, Ar', Ar" moieties.

4 Claims, 2 Drawing Sheets

TRIAZINE COMPOUNDS AND THEIR USE

This invention relates to triazine compounds and their use in the manufacture of electro-luminescent, electronic and liquid crystal devices. In particular the present invention is concerned with triazine derivatives which are capable of exhibiting a nematic discotic liquid crystal phase, a columnar liquid crystal phase and/or a columnar crystalline phase.

Mesogenic compounds which are capable of exhibiting a discotic columnar liquid crystalline phase are known as electric charge carriers for use in electro-luminescent devices. For example, D. Adam et al, Nature, volume 371, Sep. 8, 1994, pages 141 to 143 disclose that 2,3,6,7,10,11-hexahexylthiotriphenylene is capable of exhibiting a discotic liquid crystal phase and that a highly ordered helical columnar phase of this compound forms by cooling an isotropic liquid melt thereof via the discotic liquid crystal phase. Compounds of this type are suitable for transport of holes. DE-A-4343412 discloses discotic liquid crystal charge transport compounds based on a variety of molecules including triphenylene, phthalocyanine, tricycloquinazoline, perylene, decacyclene and porphyrine. DE-A-4343412 also discloses calamitic liquid crystal compounds based on oxadiazole, thiadiazole, biphenyl, terphenyl, quaterphenyl, stilbene, pyrimidine and oxazoline. DE-A-4325238 also discloses organic charge transporting compounds having liquid crystal properties based on tricycloquinazoline. C. Nuckolls et al, J. Am. Chem. Soc., 1996, volume 118, pages 3767 to 3768 and A. J. Lovinger et al, J. Am. Chem. Soc. 1998, volume 120, pages 264 to 268 describe a highly aggregated fibrous columnar phase of a coloured helicene derivative that may be especially useful for charge transport due to the apparently strong interaction of neighbouring molecular cores in the columnar stack.

D. Goldmann et al (Liquid Crystals, 1996, Vol 21, No 5, 619–623) disclose sheet-shaped mesogens based on 2,4,6-triarylamino-1,3,5-triazine, more specifically 2,4,6-tris(3,4-dialkoxyphenylamino)-1,3,5-triazines. In such compounds, the aryl substituent is connected to the triazine ring via a secondary amino group. The free hydrogen on the secondary amino group is quite reactive and so there would be a tendency for the molecule to decompose, particularly under the conditions experienced in use in electroluminescent devices.

It is an object of the present invention to provide a novel class of triazine compounds which have an electron-deficient central unit that favours transport of negative charges (electrons), which are not coloured and therefore do not absorb light, and which are chemically relatively unreactive since they do not bear reactive groups such as —NH—, and so are less susceptible to unwanted decomposition.

According to the present invention, there is provided a class of triazine compounds of the general formula:

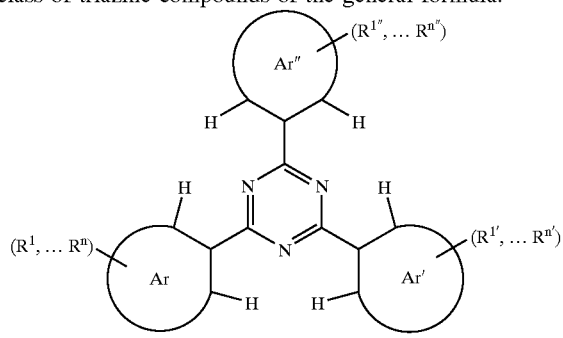

wherein Ar, Ar' and Ar" are aromatic moieties and are the same or different; each of $R^1$, $R^{1'}$, $R^{1''}$ to $R^n$, $R^{n'}$, $R^{n''}$ (hereinafter sometimes simply referred to as "groups R"), which may be the same or different, is an elongated flexible, at least partly aliphatic chain such as to impart liquid-crystalline or columnar crystalline properties to the compound; and —($R^1$, . . . , $R^n$), —($R^{1'}$, . . . , $R^{n'}$) and —($R^{1''}$, . . . , $R^{n''}$) indicate that there are up to n, n' and n" substituent groups R on the respective Ar, Ar', Ar" moieties, where n, n' and n" are integers which do not exceed the number of available substituent positions on the respective Ar, Ar', Ar" moieties.

Some of the compounds of the present invention are capable of exhibiting a columnar liquid crystal phase or a columnar soft crystalline phase which is advantageous in electro-luminescent devices due to the good charge transport properties along the director direction and the lack of pronounced grain boundaries between domains such as known from rigid crystals. Especially advantageous are those compounds of the present invention which exhibit highly ordered (soft crystalline) columnar phases such as reported by Lovinger et al (supra) and Adam et al (supra) but not by Goldmann et al (supra), due to enhanced transport in more ordered systems. An example of such a compound is 2,4,6-tris-(3,4-dinonyloxyphenyl)-1,3,5-triazine.

Furthermore, some of the compounds of the present invention are mesogenic compounds which are capable of exhibiting a discotic nematic phase at room temperature which is advantageous for use in liquid crystal devices due to their elastic properties compared to standard (calamitic) nematics, eg for flexoelectric cholesteric displays, and due to their optical and alignment properties, eg for optical compensation layers to enhance the viewing angle dependence of displays. Such compounds may be those in which R is an acyloxy group such as a ($C_5$ to $C_8$)acyloxy group.

The above property of being capable of exhibiting a columnar liquid crystal phase, columnar soft crystalline phase and/or a discotic nematic phase may be exhibited by the compound either in its pure state or when in admixture with one or more other such triazine compounds or when in admixture with one or more other compounds or both where the amount exceeds 20 wt % (more typically >50 wt %) of the mixture. Such one or more other compounds may be one or more other triazine compounds according to the present invention.

The aromatic moiety in each of Ar, Ar' and Ar" may be a single or multiple ring (fused and/or unfused) monoaromatic or heteroaromatic moiety. Conjugation of the aromatic unsaturation in Ar, Ar' and Ar" with the central triazine group, combined with the planarising action of the electronic attraction of the nitrogens and inner hydrogens in the above formula, effectively holds the three aromatic and the central triazine group in a planar (discotic) form, thereby facilitating the formation of columnar and nematic phases.

Compounds of the above-defined type have an electron-deficient central unit, because they incorporate nitrogens in the aromatic ring, and thereby facilitate the production of a liquid-crystalline and/or columnar electron transport layer for use in electro-luminescent devices. Such compounds are most preferably colourless, contain no chemically reactive groups such as eg —NH— or —OH and exhibit a liquid crystalline and/or columnar phase at room temperature. The compounds of D. Goldmann et al. (supra) contain —NH— groups.

JP-A-7-157473 and JP-A-8-199163 disclose triazine guiding materials for use in electron-transport in electro-optical devices. However, in such triazine compounds, substituent groups to the triazine contain benzoxazole, benzthiazole, benzimidazole or arylamino moieties and are not capable of exhibiting a liquid crystalline and/or columnar phase because flexible chains are lacking and, in some cases, because heteroatoms in the inner positions or the three aromatic substituents favour high torsion angles between the triazine and the substituent rings.

Some of the compounds of the present invention are rare in being discotic nematics, ie nematics with a negative birefringence. For example, 2,4,6-tris-(3,4-diacyloxyphenyl)-1,3,5-triazines where the acyl group is pentanoyl, hexanoyl, heptanoyl or octanoyl are such compounds. Known discotic nematic compounds are either very large and therefore the phase is highly viscous, or of poor chemical inertness or have very high clearing points. The compounds of D. Goldmann et al. (supra) are not reported as possessing a nematic phase.

Additionally, and especially if at least one of the groups R is polymerisable, the compound of the present invention may be a polymerisable mesogen which has potential use, for example, in the manufacture of optical viewing angle compensation films for electro-optical displays.

Preferably, the groups R are independently selected from alkyl, alkyloxy, alkylthio, alkylamino, acyl, acyloxy, acylthio, acylamino, alkyloxycarbonyl and their alkenyl and alkynyl equivalents, where the alkyl moieties may include heteroatoms and/or further aromatic moieties. It is preferred for each of the groups R to have a carbon chain length of at least about four carbons, preferably about 4 to 20.

In one series of the embodiments, the compound of the present invention has the general formula:

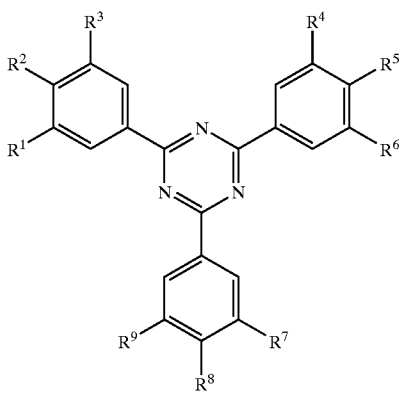

wherein $R^1$ to $R^9$ are selected from H and the above possibilities for R, provided that at least one of $R^1$ to $R^3$, at least one of $R^4$ to $R^6$ and at least one of $R^7$ to $R^9$ are independently selected from the above possibilities for R. For example, $R^1$, $R^4$ and $R^7$ may be H and the remainder may be R, eg $C_{n-1}H_{2n-1}COO$— where n is 1 or more, preferably 2 to 20. $C_{n-1}H_{2n-1}COO$— may be, for example, be n-hexanoyloxy or n-heptanoyloxy. These compounds can be conveniently produced starting with the known synthesis of triveratryltriazine from veratronitrile, followed by demethylation and esterification, according to the following reaction scheme:

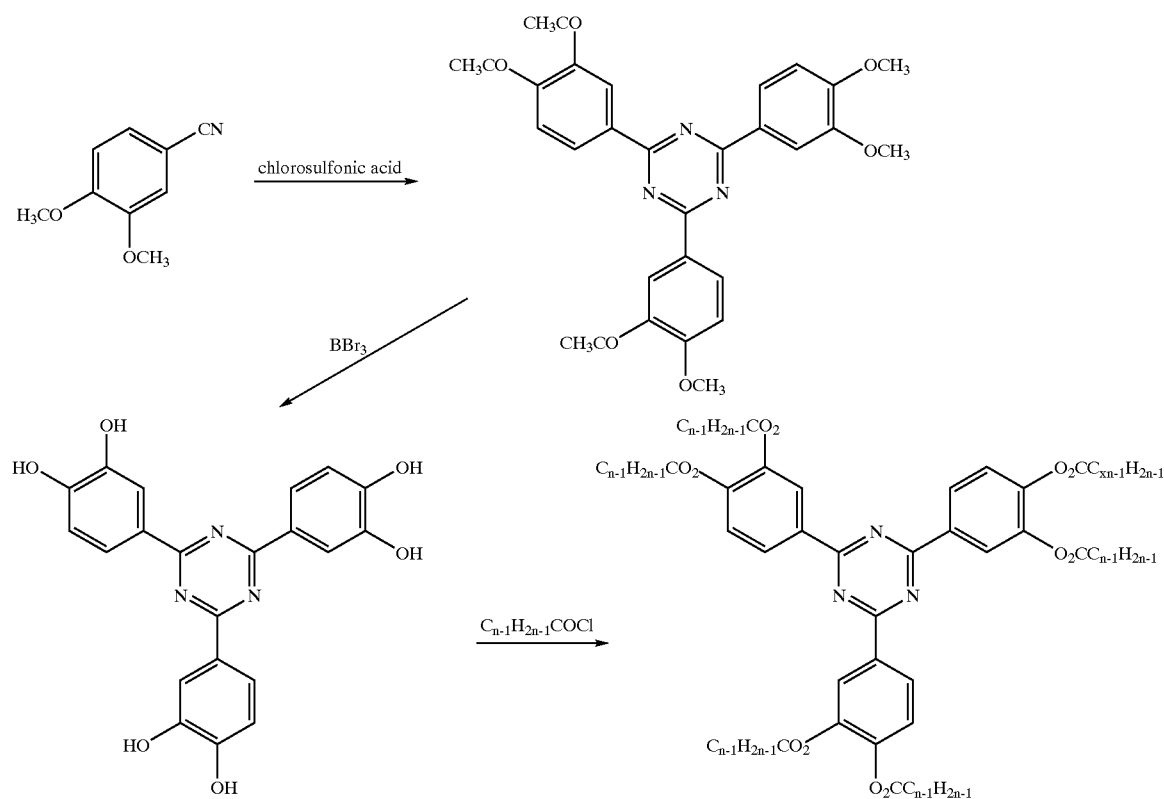

Analogous methods may be used for preparing the certain of the compounds according to the present invention having the following general formulae:
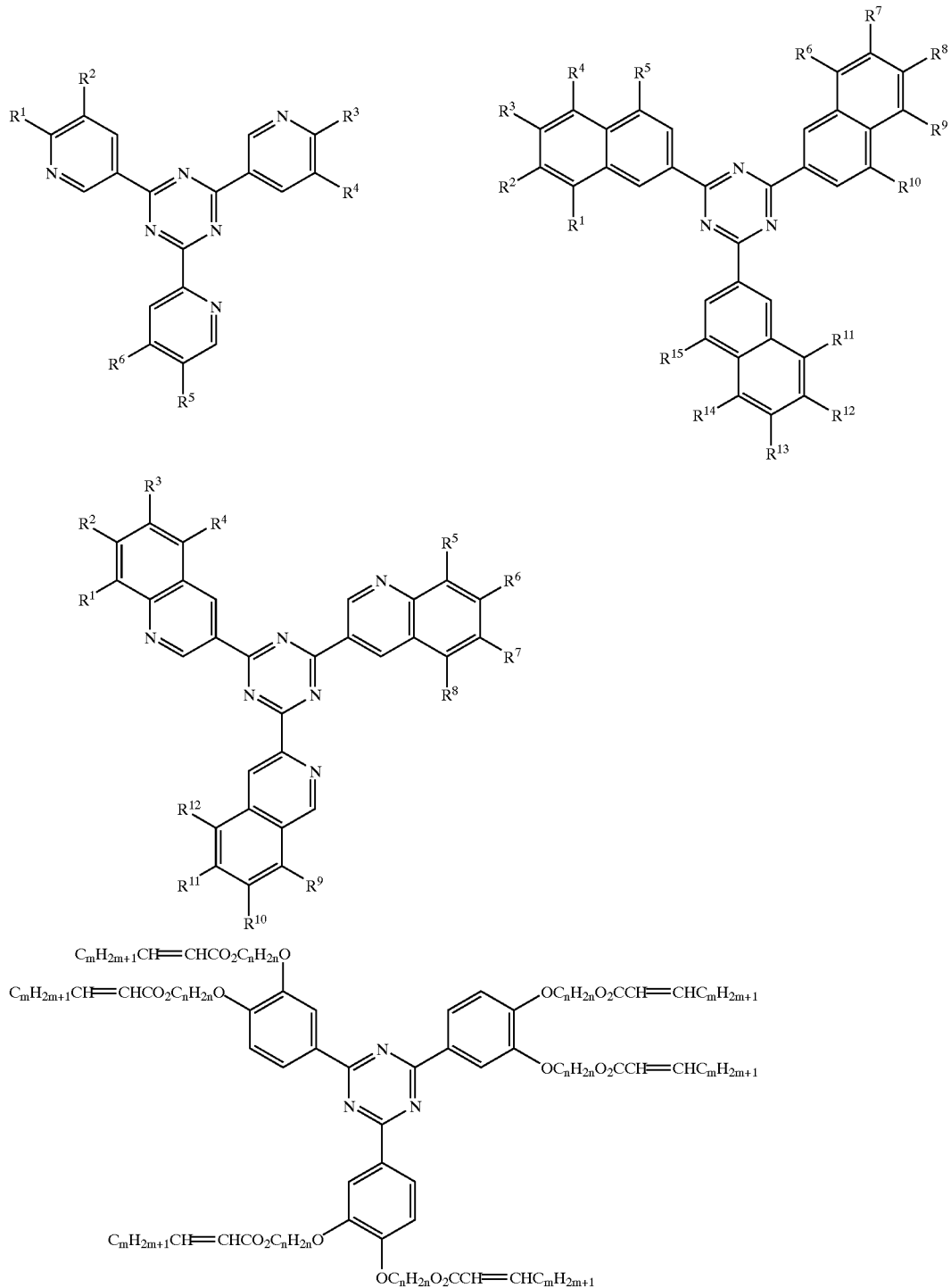

-continued

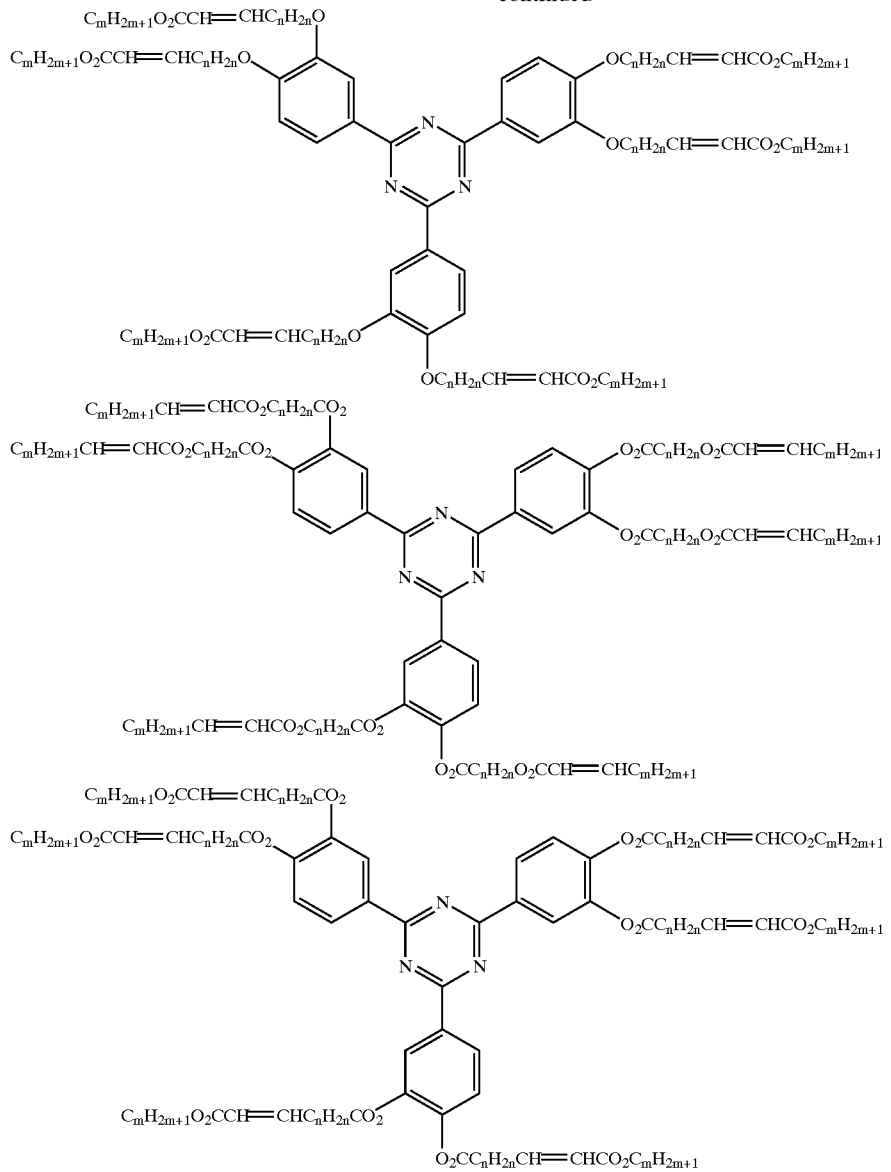

wherein $R^1$ to $R^{15}$ are independently selected from H and R (where R is as defined as in any one of claims 1 to 4), provided that at least one of the substituents on each of the aromatic moieties attached to the triazine ring is independently selected from R, n is 1 to 20 and m is 0 to 20.

The last four mentioned general formulae above contain ethylenic unsaturation and may be UV-polymerised. This is potentially useful for making optical compensation films where a layer of the triaryl-triazine is deposited, for example by spinning, onto a substrate followed by UV-polymerisation to effect cross-linking.

Figure 2:
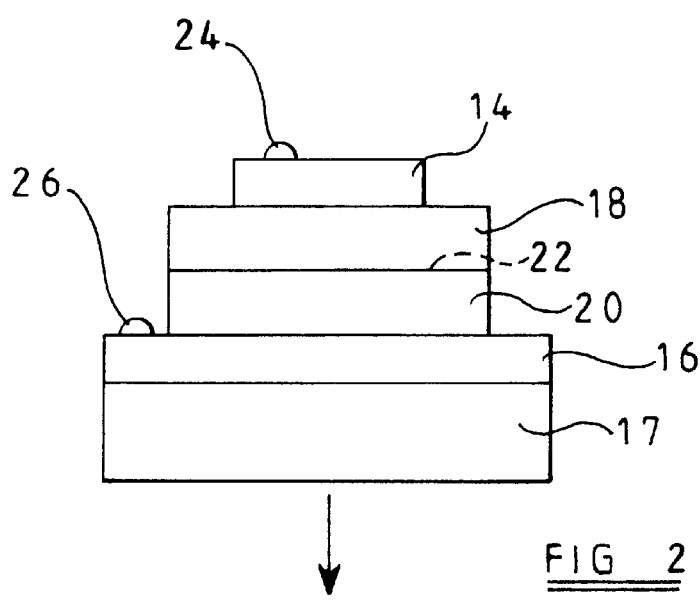
Figure 3:
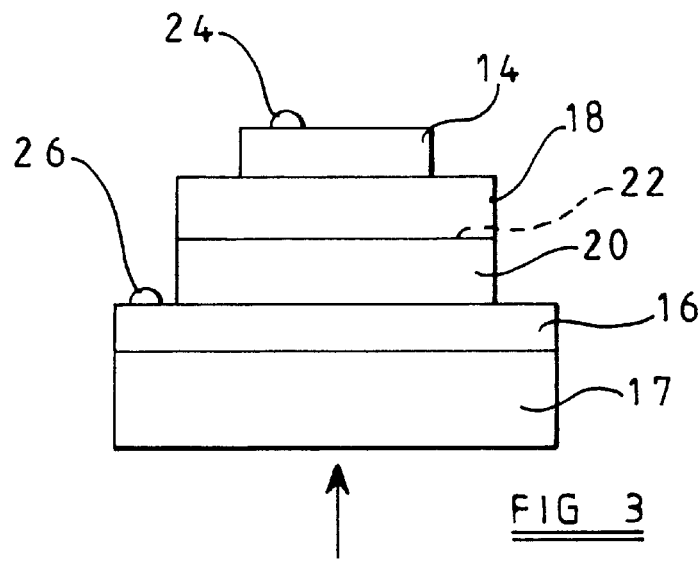
Figure 4:
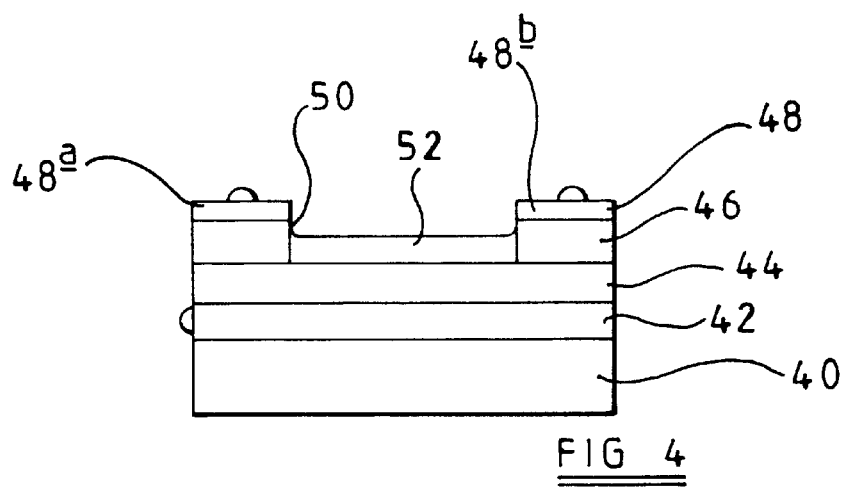
Figure 5:
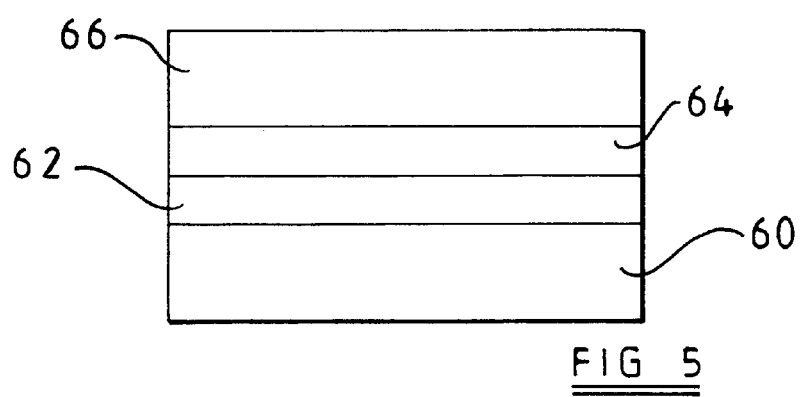

Embodiments of various devices utilising compounds according to the present invention will now be described with reference to the accompanying drawings in which:

FIG. 1 is a schematic perspective view of an organic electroluminescent device with columnar hole and electron transport layers, FIG. 2 is a schematic sectional view showing in more detail the basic structure of an electroluminescent device wherein those parts of the device which are similar to that of FIG. 1 are accorded the same reference numerals, FIG. 3 is a schematic view of a photovoltaic device incorporating at least one compound according to the present invention, FIG. 4 is a schematic view of a transistor incorporating at least one compound according to the present invention, and FIG. 5 is a schematic view of a dual layer device for use in electrophotography, e.g. a photocopier.

Referring now to FIG. 1 of the drawings, the device comprises a pair of electrodes, a metal cathode 14 and an eg ITO-on-glass anode 16 which are spaced apart so as to define a cell within which is provided a columnar electron transport layer 18, a columnar hole transport layer 20, a recombination zone 22 defined by the junction between the layers 18 and 20. The recombination zone 22 defines an electroluminescent region of the device and might be doped with luminescent dye molecules to enhance emission.

The electron transport layer 18 is thus formed from a columnar mixture that is at least partially composed of triazine compounds according to the present invention. The columnar hole transport layer 20 is formed from suitable hole transport materials such as hexaalkyl-hexabenzocoronene or hexaalkylthio-triphenylene mesogens such as disclosed by van de Craats et al (Advanced Materials, 1998, 10, No. 1 pages 36 to 38). Alternatively, the hole transport layer may be composed of conventional non-discotic materials such as mentioned by Tang and van Slyke, Applied Physics Letters 1987, 51, 913.

In use, a voltage is applied across the cell via the cathode 14 and the anode 16. This causes electrons from the cathode 14 to be transported via the layer 18 to the zone 22 and holes to be transported from the anode 16 though the layer 20 to the zone 22 where the electrons and holes combine to produce electro-luminescence.

Referring now to FIG. 2 (where parts similar to those in FIG. 1 are accorded the same reference numerals), cathode 14 is formed of silver and is connected with an electrical supply via terminal 24. The anode 16 is a layer of indium tin oxide provided on a glass substrate 17. The anode 16 is connected with an electrical supply via terminal 26.

In the device of FIG. 2, either or both of the layers 18 and 20 may incorporate one or more compounds of the present invention. One or both of these layers 18 and 20 or the recombination zone 22 between such layers may be doped with a dye or a dye mixture that emits in the desired wavelength region (e.g. visible) so that recombination of holes with electrons causes light to be emitted in the direction indicated by the arrow in FIG. 2. However, since triazines have a certain degree of electroluminescence themselves, it is considered that the use of an additional dye is optional.

Referring now to FIG. 3 of the drawings, the photovoltaic device has a similar basic structure to the device of FIG. 2 and similar parts are accorded the same reference numerals. However, in this embodiment, the dye or dye mixture is one which absorbs light in the desired wavelength region so that light entering the device in the direction of the arrow in FIG. 3 is absorbed by the dye or dye mixture to cause separation of holes and electrons and thereby produce a voltage across terminals 24 and 26.

Referring now to FIG. 4, the transistor illustrated therein is a field-effect transistor and comprises a silicon wafer 40 on which is provided an n-Si electrode 42 forming a gate of the transistor. A silicon dioxide layer 44 is provided over the gate 44. Over the layer 44 is a layer 46 of poly-n-Si. An aluminium layer 48 is deposited on the layer 46. The layers 46 and 48 are etched to form a channel 50 and so as to define source and drain electrodes 48a and 48b, respectively, of the transistor. A layer 52 of at least one triazine compound according to the present invention is provided in the channel 50, thus providing a conduction channel of the transistor. The resultant field effect transistor operates in a per se known way. Application of a positive or negative voltage to the gate 42 causes accumulation or depletion of electrons, respectively, in the channel 52 thereby making or breaking the electrical connection between the source and drain electrodes 48a and 48b.

Referring now to FIG. 5, the device illustrated therein comprises a substrate 60 upon which are provided an electrode 62, a charge-generating layer 64 and a charge-transport layer 66. The charge-transport layer 66 contains at least one triazine compound according to the present invention. The charge-generating layer 64 incorporates absorbing dyes. In an alternative embodiment; the layers 64 and 66 are combined into a single photoreceptor layer. The device operates in a per se well known way to enable an image to be captured electrostatically.

EXAMPLES

A method of synthesising 2,4,6-tris-(3,4-diacyloxyphenyl)-1,3,5-triazines (where acyl=acetyl, propionyl, butyryl, pentanoyl, hexanoyl, heptanoyl, octanoyl, nonanoyl, decanoyl) and 2,4,6-tris-(3,4-dialkyloxyphenyl)-1,3,5-triazines (where alkyl=pentyl, hexyl, heptyl, octyl, nonyl, decyl) will now be described.

1) 3,4-Dimethoxybenzonitrile (25 g) is dissolved in dry chloroform (33 ml). Chlorosulfonic acid (33 ml) is gradually added under ice bath cooling and magnetic stirring. After 15 min, the red mixture is cautiously poured into an ice-water mixture. The precipitate is collected, washed with ethanol and recrystallised from a large amount of boiling pyridine. Yield: c. 30% white 2,4,6-tris-(3,4-dimethoxyphenyl)-1,3,5-triazine.

2) To a suspension of this trisdimethoxyphenyltriazine (20 g) in dry chloroform (500 ml), boron tribromide (100 g) is slowly added under magnetic stirring. The mixture first turns red, then yellow or orange. After stirring for 4 h, the mixture is poured into water (500 ml). The greenish precipitate is filtered off, dissolved in a 1:1 mixture of ethanol and ethyl acetate, and reprecipitated by adding hexane. Yield: c. 60% yellow 2,4,6-tris-(3,4-dihydroxyphenyl)-1,3,5-triazine.

3a) This trisdihydroxyphenyltriazine is per-esterified with 10 moles per mole triazine of the appropriate acyl chloride (acetyl, propionyl, butyryl, pentanoyl, hexanoyl, heptanoyl, octanoyl, nonanoyl, decanoyl) in pyridine (50 ml per g triazine). After stirring for 4h at room temperature, water is added and the product extracted with ethyl acetate. The ethyl acetate phase is washed with water, dried over magnesium sulphate, and the solvent is evaporated. Chromatography in ethyl acetate (acetyl, propionyl and butyryl esters) or dichloromethane (pentanoyl to decanoyl esters) on silica gel followed by recrystallisation in isopropanol yields the desired 2,4,6-tris-(3,4-diacyloxyphenyl)-1,3,5-triazine. Yields: >30%.

Representative 300 MHz NMR of 2,4,6-tris-(3,4-dioctanoyloxyphenyl)-1,3,5-triazine (in deutero-chloroform with tetramethylsilane as internal standard): δ=0.84–0.95 (m, 18H, —O$_2$CCH$_2$CH$_2$(CH$_2$)$_4$C$\underline{H}_3$), 1.23–1.51 (m, 48H, —O$_2$CCH$_2$CH$_2$(C$\underline{H}_2$)$_4$CH$_3$), 1.71–1.86 (m, 12H, —O$_2$CCH$_2$C$\underline{H}_2$(CH$_2$)$_4$CH$_3$), 2.58 and 2.63 (each: t, 7 Hz, 6H, —O$_2$CC$\underline{H}_2$CH$_2$(CH$_2$)$_4$CH$_3$), 7.40 (d, 8.5 Hz, 3H, aromatic), 8.49 (d, 2 Hz, 3H, aromatic), 8.63 (dd, 8.5 Hz and 2 Hz, 3H, aromatic).

The 2,4,6-tris-(3,4-diacyloxyphenyl)-1,3,5-triazines thus synthesised exhibit the following phase behaviour as determined by polarising microscopy of thin samples between glass slides:

- acyl=acetyl: crystalline, melting under decomposition at 250 to 260° C.
- acyl=propionyl: crystalline, melting point 198° C.
- acyl=butyryl: crystalline, melting point 161° C.
- acyl=pentanoyl: crystalline, melting point 110° C., a monotropic discotic nematic phase appears on cooling below 58° C.
- acyl=hexanoyl: crystalline, melting point 87° C., a monotropic discotic nematic phase appears on cooling below 59° C.
- acyl=heptanoyl: crystalline, melting point 85° C., a monotropic discotic nematic phase appears on cooling below 52° C.
- acyl=octanoyl crystalline, melting point 68° C., a monotropic discotic nematic phase appears on cooling below 39° C.
- acyl=nonanoyl: no anisotropic phase could be observed at or above 20° C. when cooling down the isotropic liquid from 100° C. between glass slides.

acyl=decanoyl: no anisotropic phase could be observed at or above 20° C. when cooling down the isotropic liquid from 100° C. between glass slides.

Mixture formulation: To suppress crystallisation, a 1 mol:1 mol:1 mol:1 mol mixture of the pentanoyl, hexanoyl, heptanoyl and octanyl derivatives was prepared by mixing the derivatives together to form an intermolecular mixture. Crystallisation at room temperature is significantly delayed, occurring generally only after many hours, thereby showing that mixing is an effective tool to suppress crystallisation. The nematic phase appears when cooling to about 51° C. In thin films as used in organic electro-luminescent devices, it is presumed that further suppression of crystallisation will take place.

3b) The above trisdihydroxyphenyltriazine is per-etherified by refluxing for 4 h with 15 moles per mole triazine of the appropriate alkyl bromide (pentyl, hexyl, heptyl, octyl, nonyl, decyl), potassium carbonate (10 g per g triazine) and potassium iodide (0.5 g per g triazine) in dimethylformamide (100 ml per g triazine). The mixture is then poured into water, the product is extracted with a 2:1 mixture of hexane and dichloromethane, the organic phase is washed three times with water and dried over magnesium sulphate. The organic solvent is evaporated and the product is dissolved in a 1:1 ethanol-dichloromethane mixture and reprecipitated by evaporating most of the dichloromethane. Yields: >40%.

Representative 300 MHz NMR of 2,4,6-tris-(3,4-dinonyloxyphenyl)-1,3,5-triazine (in deutero-chloroform with tetramethylsilane as internal standard): δ=0.83–0.93 (m, 18H, —OCH$_2$CH$_2$(CH$_2$)$_6$CH$_3$), 1.21–1.59 (m, 72H, —OCH$_2$CH$_2$(CH$_2$)$_6$CH$_3$), 1.83–1.96 (m, 12H, —OCH$_2$CH$_2$(CH$_2$)$_6$CH$_3$), 4.11 and 4.19 (each: t, 7 Hz, 6H, —OCH$_2$CH$_2$(CH$_2$)$_6$CH$_3$), 7.02 (d, 8.5 Hz, 3H, aromatic), 8.27 (d, 2 Hz, 3H, aromatic), 8.34 (dd, 8.5 Hz and 2 Hz, 3H, aromatic).

The 2,4,6-tris-(3,4-dialkyloxyphenyl)-1,3,5-triazines thus separately synthesised exhibit the following phase behaviour as determined by polarising microscopy of thin samples between glass slides:

alkyl=pentyl: crystalline, melting point 144° C.
alkyl=hexyl: crystalline, melting point 130° C.
alkyl=heptyl: crystalline, melting point 125° C.
alkyl=octyl: crystalline, melting point 119° C.
alkyl=nonyl: a fibrous phase with an optical texture such as described for the fibrous columnar phase of a hexa-helicene derivative by A. J. Lovinger et al., Journal of the American Chemical Society 1998, 120, pages 264 to 268 is observed below the transition temperature to the isotropic liquid of 117° C.; no other anisotropic phase could be observed at or above 20° C.
alkyl=decyl: a fibrous phase with an optical texture such as described for the fibrous columnar phase of a hexa-helicene derivative by A. J. Lovinger et al., Journal of the American Chemical Society 1998, 120, pages 264 to 268, is observed below the transition temperature to the isotropic liquid of 116° C.; no other anisotropic phase could be observed at or above 20° C.

3c) The above trisdihydroxyphenyltriazine is esterified with a 1:1:1:1 molar mixture of pentanoyl, hexanoyl, heptanoyl and octanoyl chlorides to produce an intramolecular ester mixture as opposed to the intermolecular mixture as described in 3a) above. The resultant intramolecular ester mixture yields a nematic phase when cooling the isotropic liquid to room temperature (20° C.), and in the course of hours this nematic phase transforms to a columnar phase which, depending upon the sample, possesses either the typical flower-like texture of columnar liquid crystals with planar alignment or the typical black between crossed polarisers of homeotropic alignment. Heating the nematic state reveals a nematic to isotropic transition temperature of about 50° C., whilst heating the columnar state yields a columnar to isotropic transition at a few degrees above 50° C.

To induce appropriate phase behaviour (eg to stabilise a liquid crystalline or soft crystalline columnar phase), the triazines of the present invention may be mixed with other compounds, eg electron-richer, column-forming discotics such as hexaalkoxy- or hexaalkylthio-triphenylenes or -truxenes. For example, 1 mol:1 mol and 3 mol:1 mol mixtures of 2,4,6-tris-(3,4-dihexanoyloxyphenyl)-1,3,5-triazine with 2,3,6,7,10,11-hexakis-(hexylthio)-triphenylene were found to exhibit columnar phases that appear on cooling the isotropic liquid down from elevated temperature.

The triazines of the present invention have, in the appropriate environment, the following potential uses:
a) Charge transporters and/or light emitters in optical-electronic devices,
b) In twisted nematic, flexoelectric cholesteric (if chiral or chirally doped), pi cells and other liquid crystal devices,
c) Charge transporters and/or light emitters and/or light absorbers in other optical and/or electrical devices such as photovoltaic cells, photocopiers or organic transistors.

What is claimed is:
1. A triazine compound of the formula:

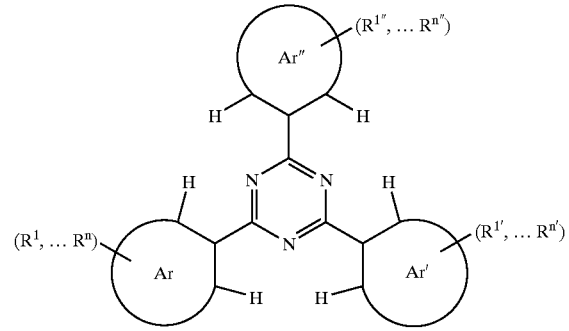

wherein Ar, Ar' and Ar" are single or multiple, fused and/or unfused ring moieties, which moieties are aromatic or are selected from 3-pyridyl, 2-naphthyl and 3-quinolyl, which are conjugated to the triazine core and are the same or different;

each of $R^1$, $R^{1'}$, $R^{1''}$ to $R^n$, $R^{n'}$, $R^{n''}$, which may be the same or different, is an elongated flexible, aliphatic or aryl-substituted aliphatic chain which imparts liquid-crystalline or columnar crystalline properties to the compound or mixtures of the compounds; and —($R^1$, . . . , $R^n$), —($R^{1'}$, . . . , $R^{n'}$), and —($R^{1''}$, . . . , $R^{n''}$) indicate that there are up to n, n' and n" substituent groups R on respective Ar, Ar', Ar" moieties, where n, n' and n" are integers which do not exceed a number of available substituent positions on the respective Ar, Ar', Ar" moieties, wherein each of $R^1$, $R^{1'}$, $R^{1''}$ to $R^n$, $R^{n'}$, $R^{n''}$ is independently selected from alkenyl, alkenyloxy, alkenylthio, alkenylamino, alkenyloxycarbonyl, and alkenyl equivalents of acyl, acyloxy, acylthio, and acylamino, where the alkenyl moieties may include further aromatic moieties.

2. A compound as claimed in claim 1, wherein each of the groups R has a carbon chain length of at least four carbon atoms.

3. A compound having the formula:

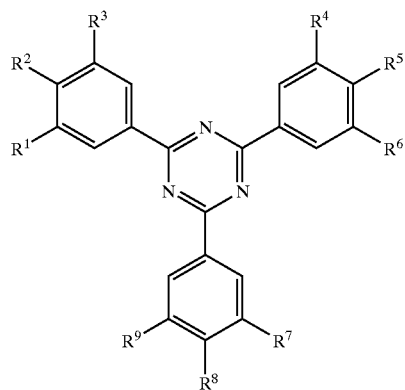

wherein each of $R^1$ to $R^9$ which may be the same or different is independently selected from H and R, wherein R is an elongated flexible, aliphatic or aryl-substituted aliphatic chain which imparts liquid-crystalline or columnar crystalline properties to the compound or mixtures of the compounds, provided that at least one of $R^1$ to $R^3$, at least one of $R^4$ to $R^6$ and at least one of $R^7$ to $R^9$ are independently selected from R, wherein each R is independently selected from alkenyl, alkenyloxy, alkenylthio, alkenylamino, alkenyloxycarbonyl, and alkenyl equivalents of acyl, acyloxy, acylthio, and acylamino, where the alkenyl moieties may include further aromatic moieties.

4. A compound having one of the following formulas:

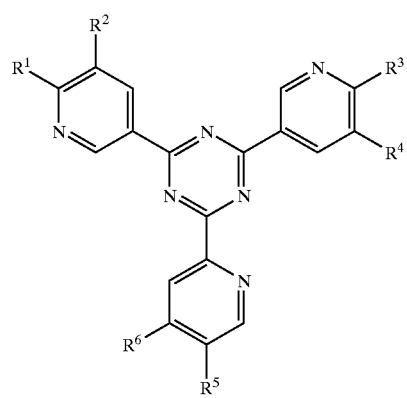

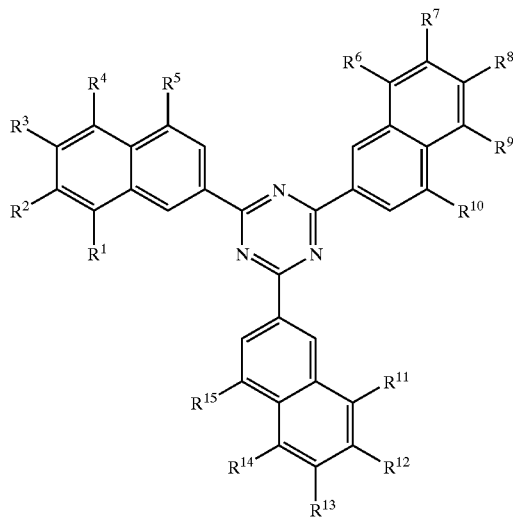

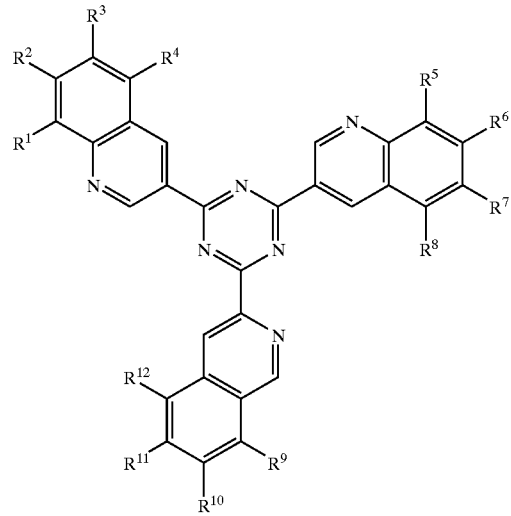

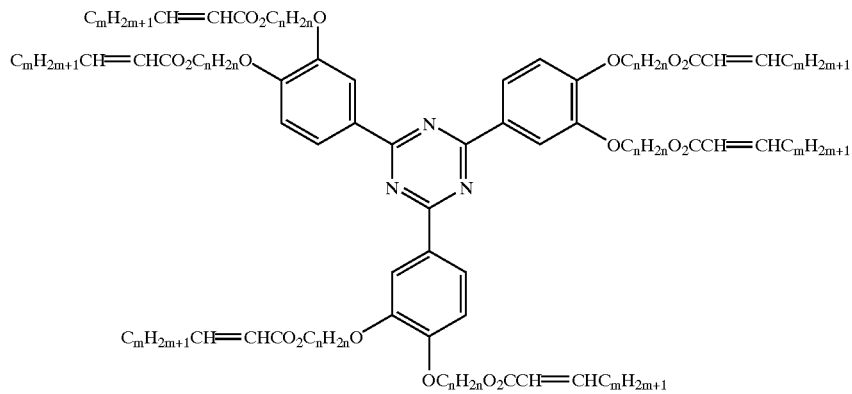
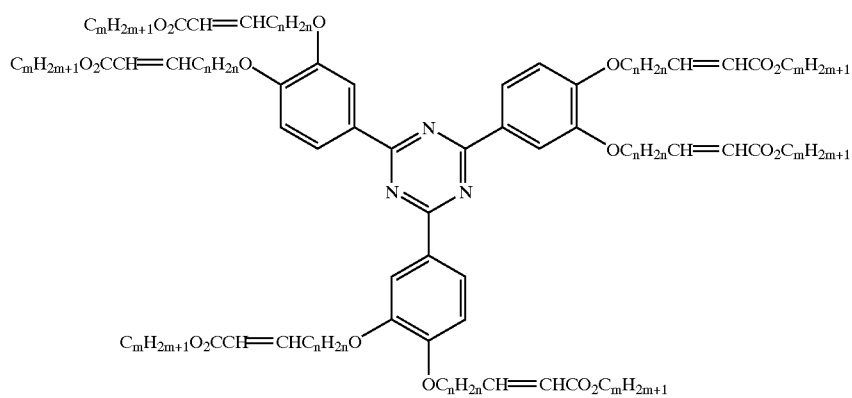
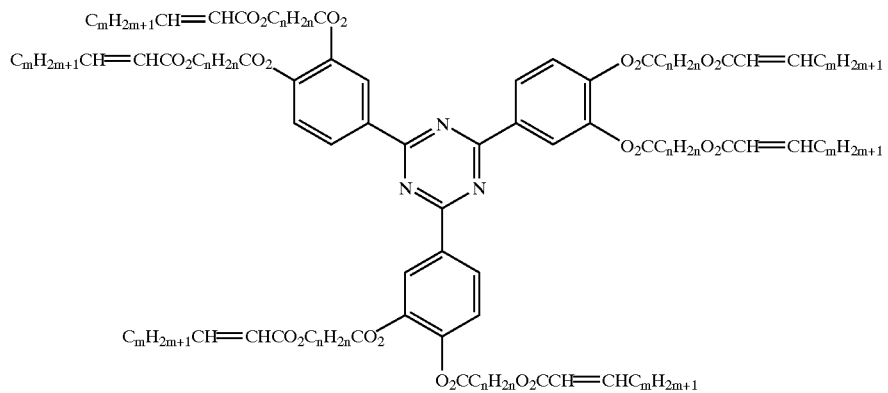
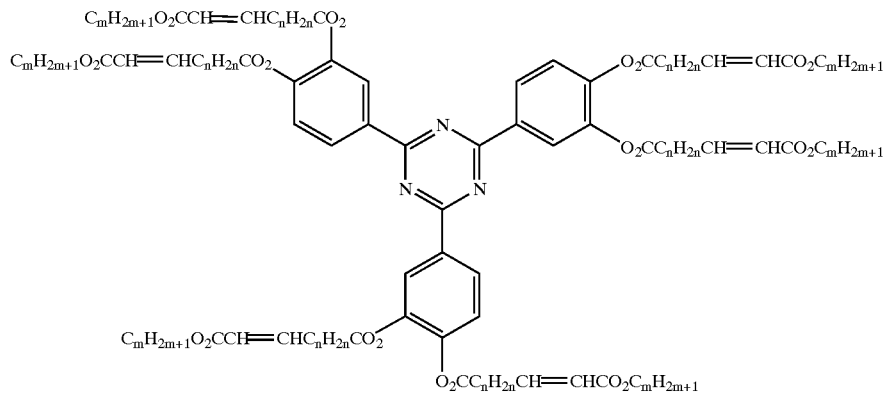

wherein each of $R^1$ to $R^{15}$ which may be the same or different, is independently selected from H and R, wherein R is an elongated flexible, aliphatic or aryl-substituted aliphatic chain such as to impart liquid-crystalline or columnar crystalline properties to the compound or mixtures of the compounds, provided that at least one of the substituents on each of the single or multiple, fused and/or unfused ring moieties, which moieties may be aromatic, attached to the triazine ring is independently selected from R, and wherein n is 1 to 20 and m is 0 to 20, wherein each R is independently selected from alkenyl, alkenyloxy, alkenylthio, alkenylamino, alkenyloxycarbonyl, and alkenyl equivalents of acyl, acyloxy, acylthio, and acylamino, where the alkenyl moieties may include further aromatic moieties.

\* \* \* \* \*